United States Patent [19]

Obser et al.

[11] 4,004,152

[45] Jan. 18, 1977

[54] APPARATUS FOR MONITORING A MOVING WEB OF MATERIAL FOR FAULTS

[75] Inventors: Werner Obser, Geretsried; Gernot Pinior, Olching, both of Germany

[73] Assignee: Erwin Sick GmbH Optik-Elektronik, Waldkirch, Germany

[22] Filed: July 7, 1975

[21] Appl. No.: 593,399

[30] Foreign Application Priority Data

July 12, 1974 Germany .......................... 2433683

[52] U.S. Cl. ............................... 250/562; 250/572; 356/200
[51] Int. Cl.² ........................................ G01N 21/32
[58] Field of Search .......... 250/571, 572, 562, 563, 250/216, 227, 226; 356/237, 238, 239, 199, 200

[56] References Cited

UNITED STATES PATENTS

| | | | |
|---|---|---|---|
| 3,060,319 | 10/1962 | Greunke ............................ | 250/571 |
| 3,317,738 | 12/1970 | Piepenbrink et al. ......... | 250/572 X |
| 3,331,963 | 7/1967 | Lippke ............................... | 250/563 |
| 3,574,469 | 4/1971 | Emerson ....................... | 250/571 X |
| 3,784,832 | 1/1974 | Sewell ............................... | 250/226 |

Primary Examiner—Alfred E. Smith
Assistant Examiner—T. N. Grigsby
Attorney, Agent, or Firm—Townsend and Townsend

[57] ABSTRACT

Apparatus for inspecting a web of material for faults or aberrations which affect the remission and reflection of light incident on the material. A first cylindrical lens focuses light scanned over the length of the lens on the material and intercepts light which is remitted by the material. A first light conducting rod is positioned outside the angle of reflection of the light by the material and captures the remitted light. It is disposed on the side of the first cylindrical lens opposite the material so that the remitted light first passes through the first cyclindrical lens. A second cylindrical lens is positioned between the first rod and the first lens for concentrating the remitted light on an envelope region of the first rod. A second light conducting rod captures light reflected by the material and is positioned within the angle of reflection of the light by the material. Photo-sensitive devices are in light communication with at least one end face of each light conducting rod and they generate electrical output signals that are responsive to the remitted and the reflected light captured by the first and second light conducting rods. Means for logically associating the output signals is also provided.

14 Claims, 3 Drawing Figures

APPARATUS FOR MONITORING A MOVING WEB OF MATERIAL FOR FAULTS

The invention relates to apparatus for monitoring a moving web of material for faults which influence the remission and/or reflection of an incident transmitted light ray, wherein a transmitted light ray, scanning across the width of the web of material transversely to the direction of movement of the web, is concentrated onto the web by a cylindrical lens and light thrown back by the web is cast onto an optical fibre or light conducting rod, at the end face or faces of which respectively one or two photo-electric devices are arranged.

It is already known to scan webs of material transversely to their direction of movement, for example by a laser ray whilst a cylindrical lens arranged in the proximity of the web of material and extending in the scanning direction preferably further concentrates the transmitted light onto a point of the web of material. Light thrown back by the web is then cast onto an optical fibre likewise arranged parallel to the scanning direction, such as is described, e.g., in the German Offenlegungsschriften No. 2,115,979, 2,150,634, and 2,312,944. Such optical fibres have the property that light which strikes their envelope region is conducted by scatter effects and total reflection to photo-electric receiver devices provided at one or at both end faces, where it can then be measured.

An object of the invention is to develop the known apparatus further so that the significance of the electrical signals obtained is increased and better differentiation is therefore possible between different types of detected faults.

In order to achieve this object, the invention provides two optical fibres, of which one receives light radiated at the angle of reflection with respect to the transmitted light ray, and the other receives only light remitted outside the angle of reflection. According to the invention, therefore, the apparatus makes two signals available, of which the one is a function of the reflectivity, and the other a function of the remissivity, of the point of the web of material struck by the transmitted ray. In this way two measured quantities are available for the determination of a fault. Preferably, by a logical association of the output signals from the photo-electric devices at the ends of the optical fibres, a better conclusion as to the type of fault can also be drawn automatically. For this purpose the invention is based on the discovery that superficial and material faults influence the reflected and remitted luminous flux differently, which fact is utilised in the apparatus according to the invention.

It is particularly advantageous if the remitted light is taken substantially counter to the direction of incidence of the transmitted light ray, because by this means the optical system can be considerably simplified.

In a preferred embodiment it is provided that the transmitted light ray and remitted light are captured by apertures divided along the longitudinal axis of a cylindrical lens and that behind the first cylindrical lens there is arranged a narrower second cylindrical lens which concentrates the remitted light onto the receptive envelope region of the second optical fibre. Furthermore, the reflected ray is preferably concentrated by a third cylindrical lens onto the receptive envelope region of the first optical fibre.

The light transmitting member particularly suitable for the purposes of the present invention is described in the simultaneously filed, co-pending application by the same inventors for APPARATUS FOR MONITORING A WEB OF MATERIAL, the disclosure of which is hereby incorporated in the present application.

The invention will be described herein below, by way of illustration with reference to the accompanying drawings, wherein.

According to drawings, a web of material 12 moves past beneath the optical apparatus according to the invention in the direction of the arrow $f$.

Figure 1:
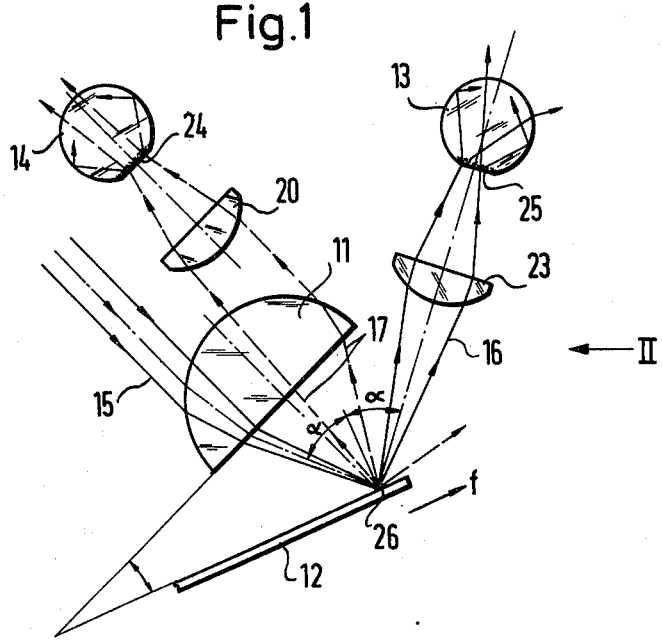
FIG. 1 shows a schematic side elevation of an apparatus according to the invention.
Figure 2:
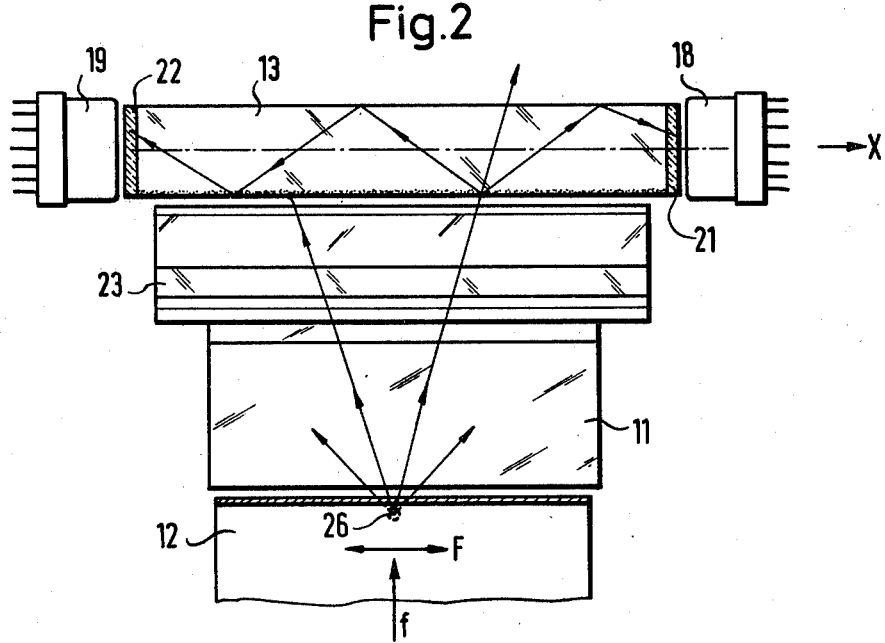
FIG. 2 shows an elevation of the apparatus according to the invention in the direction of the arrow II.

A transmitted light ray 15, generated e.g., according to the co-pending application mentioned above, by an incandescent lamp or xenon lamp and a laser, is focused or concentrated by a cylindrical lens 11 extending transversely to the direction of movement $f$ of the web 12, and in fact solely through the left-hand section of the lens in FIG. 1 onto a point 26 of the web of material 12. The transmitted light ray 15 scans the web of material continuously at right angles to its direction of movement, i.e., in the direction of the double arrow F according to FIGS. 2 and 3.

The right-hand half of the cylindrical lens 11 in FIG. 1 serves to receive and to render parallel the light 17 remitted by the web of material 12. The cylindrical lens is therefore utilised for the transmitted and received light by pupil division. On the left-hand side above the cylindrical lens 11, a further cylindrical lens 20 is arranged parallel to the first mentioned one, and concentrates the whole cross-section of the bundle of parallel light received onto the receptive envelope scattering region 24 (FIG. 2) of an optical fibre or light conducting rod 14. According to FIGS. 2 and 3, the light falling onto the envelope region 24 passes by scatter and total reflection onto two photo-electric devices 19, 18, arranged at the end faces, which may be e.g., photo-multipliers. Appropriate colour filters 21, 22, are further arranged between the end faces of the optical fibre 14 and the photo-multipliers 18, 19.

Figure 3:
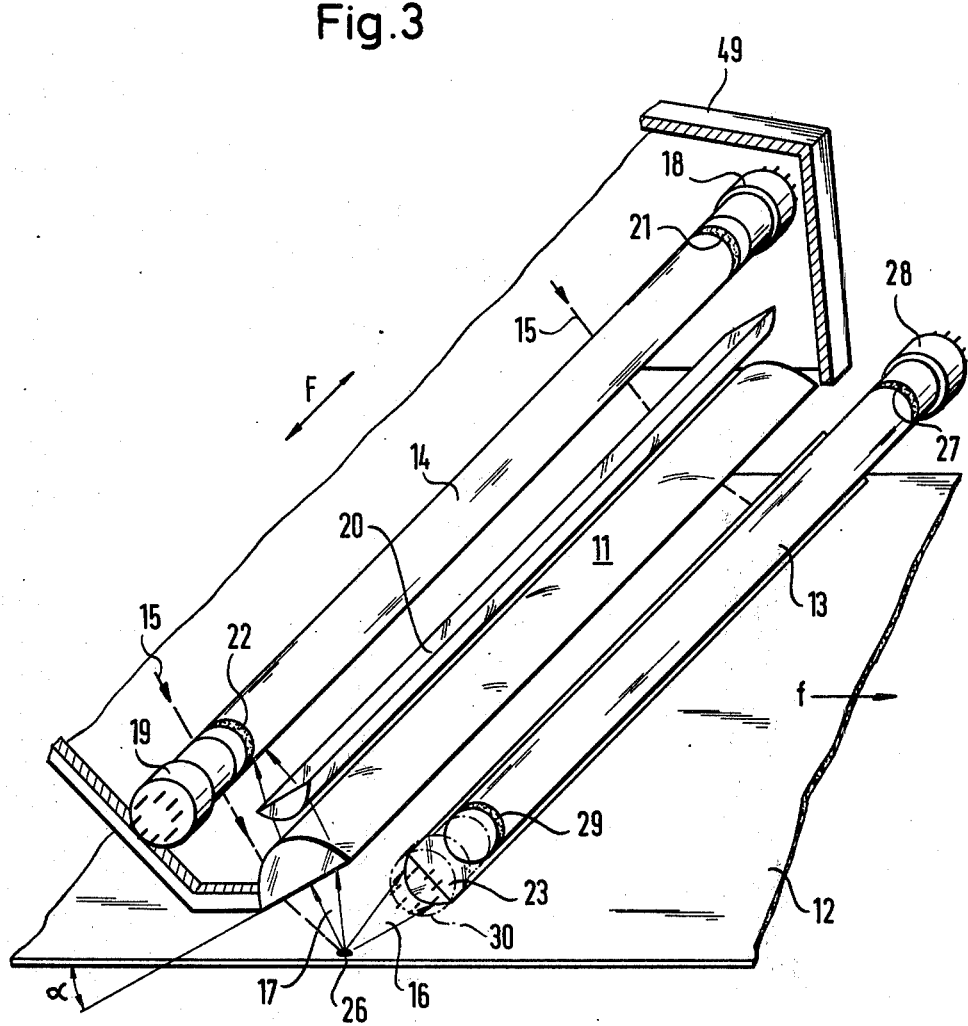
FIG. 3 shows a perspective view of the same apparatus.

Let us assume that the transmitted light ray strikes the material web 12 at the angle of incidence alpha; then, according to the invention, there is arranged at the equal and opposite angle of reflection alpha angle a further optical receiver device which receives the reflected fraction 16 of the incident light. This device comprises a cylindrical lens 23 which extends parallel to the other two cylindrical lenses 11, 20, and directs the reflected light 16 onto the receptive envelope scattering surface 25 of a further optical fibre or light conducting rod 13. The latter is constructed analogously to the optical fibre 14, and, as FIG. 3 shows, also carries colour filters 27, 29, and photo-multipliers 28, 30, at its end faces. In order to illustrate the cylindrical lens 23, in FIG. 3, the photo-multiplier 30 is merely indicated by chain dotted lines.

The entire arrangement is accommodated in a housing 49 shown fragmented. Whereas the photo-multipliers 18, 19 on the optical fibre 14 supply a measure of the remissivity of the fault 26 of the web of material 12 struck by the transmitted light ray, a signal which is representative of the reflectivity of the point 26 can be obtained from the photo-electric devices 28, 30 at the end faces of the optical fibre 13.

Thus, with only one photo-multiplier, e.g., 18, 28, on each optical fibre, two electrical signals are available, namely a remission signal and a reflection signal. A differentiated statement as to the character of the fault 26 detected is possible by this means.

Preferably, however, photo-multipliers 18, 19 and 28, 30 respectively, which are e.g., sensitive to different spectrum regions due to interposed colour filters 21, 22 and 27, 29, are used at both ends of each of the two optical fibres 13, 14. By this means the remissivity and reflectivity in the different spectrum regions, (e.g., red and green) can also be determined. Altogether therefore, four electrical signals are available for the characterisation of the fault 26 scanned.

The optical combination of the cylindrical lenses and optical fibres illustrated makes possible, particularly in the axial direction, large receiving angles (apertures), which also have a favourable effect upon the signal structure of the whole receiving device. For the detection of colour differences, the photo-multipliers 18, 19 and 28, 30 at the two end faces of the optical fibres 13 and/or 14 may also possess cathodes of different colour sensitivities. Further spectral differentiation can be made by this means. With the colour filters 21, 22 and 27, 29, illustrated, the light reaching the photo-multipliers can be divided into a favourable range with regard to its spectral composition.

What is claimed is:

1. Apparatus for inspecting a substantially flat surface portion of a material for faults or aberrations which affect the remission and reflection of a light ray incident on the material, the apparatus comprising: a cylindrical lens positioned in the path of the light ray for focusing the light ray on the surface portion of the material and for intercepting light from the light ray which is remitted by the material; means for scanning the light ray over the length of the cylindrical lens to thereby scan the light ray across the surface portion of the material; a light conducting rod for capturing light from the light ray remitted by the material, the light conducting rod being positioned on the side of the cylindrical lens opposite the material so that remitted light captured by the rod first passes through the cylindrical lens; and means in light communication with at least one end face of the light conducting rod for generating an electrical output signal responsive to the remitted light captured by the rod.

2. Apparatus according to claim 1 wherein the first lens includes a plurality of serially arranged optical apertures spaced over the length of the lens for passage of the light ray and of the remitted light therethrough.

3. Apparatus according to claim 2 wherein the light conducting rod is positioned so that it captures light remitted by the material in the direction of incidence of the light ray.

4. Apparatus according to claim 1 including a second cylindrical lens positioned between the first mentioned cylindrical lens and the rod for concentrating remitted light on an envelope region of the rod.

5. Apparatus according to claim 4 including a second light conducting rod for capturing light from the light ray reflected by the material, the second rod being positioned within the angle of reflection of the light ray by the material; a third cylindrical lens disposed between the material and the second rod for concentrating reflected light on an envelope region of the second rod; and means in light communication with at least one end face of the second rod for generating electrical output signals responsive to the reflected light captured by the second rod.

6. Apparatus according to claim 1 wherein the photosensitive devices are sensitive to different spectral regions.

7. Apparatus according to claim 6 including a light source comprising a laser and a xenon high pressure lamp and wherein the light ray is a mixture of light from the laser and the lamp.

8. Apparatus according to claim 7 wherein the laser is a He-Ne gas laser.

9. Apparatus for inspecting a substantially flat surface portion of a material for faults or aberrations which affect the remission and reflection of a light ray incident on the material, the apparatus comprising: a cylindrical lens positioned in the path of the light ray for focusing the light ray on the material and for intercepting light from the light ray which is remitted by the material; means for scanning the light ray across the surface portion of the material; a first light conducting rod for capturing light from the light ray remitted by the material, the first rod being positioned on the side of the cylindrical lens opposite the material so that remitted light captured by the first rod first passes through the cylindrical lens; a second light conducting rod for capturing light from the light ray reflected by the material, the second rod being positioned within the angle of reflection of the light ray by the material; and a photo-sensitive device in light communication with at least one end face of each light conducting rod for generating electrical output signals responsive to the remitted and reflected light captured by the first and the second light conducting rods, respectively.

10. Apparatus according to claim 9 including means for logically associating the electrical output signals of the photosensitive devices at the end faces of the light conducting rods.

11. Apparatus according to claim 9 wherein the cylindrical lens includes a plurality of optical apertures serially arranged over the longitudinal axis of the lens through which the light ray and the remitted light pass; and including a second cylindrical lens positioned between the first lens and the first light conducting rod and formed to concentrate the remitted light onto an envelope region of the first rod.

12. Apparatus according to claim 9 including a third cylindrical lens for concentrating the reflected light onto an envelope region of the second rod.

13. Apparatus according to claim 9 wherein the first light conducting rod is positioned so that it captures light remitted by the material in the direction of incidence of the light ray.

14. Apparatus for inspecting a substantially flat surface portion of a material for faults or aberrations which affect the remission and reflection of a light ray incident on the material, the apparatus comprising: a first cylindrical lens positioned in the path of the light ray on the surface portion of the material and for intercepting light from the light ray which is remitted by the material; the cylindrical lens including a plurality of optical apertures spaced over the length of the lens for passage of the light ray and of the remitted light therethrough; means for scanning the light ray over the length of the cylindrical lens so that the light ray sequentially passes through the apertures and is thereby scanned across the material; a light conducting rod positioned outside the angle of reflection of the light ray by the material and so that it captures light from the light ray remitted by the material in the direction from which the light ray strikes the material, the light conducting rod being positioned on the side of the cylindrical lens opposite the material so that remitted light captured by the rod first passes through the cylindrical lens; a second cylindrical lens positioned between the first cylindrical lens and the rod for concentrating remitted light on an envelope region of the rod; and means in light communication with at least one end face of the light conducting rod for generating an electrical output signal responsive to the remitted light captured by the rod.

* * * * *